(12) United States Patent
Hanashiro et al.

(10) Patent No.: US 6,490,937 B2
(45) Date of Patent: Dec. 10, 2002

(54) EXHAUST GAS SAMPLING APPARATUS

(75) Inventors: Noriyuki Hanashiro, Suzuka (JP);
Atsushi Shibata, Suzuka (JP);
Kyoshuke Sasaki, Suzuka (JP);
Mamoru Matsuyama, Suzuka (JP);
Keisuki Obara, Suzuka (JP); Shigeru Yanagihara, Tokyo (JP); Shuta Yamawaki, Tokyo (JP)

(73) Assignees: Honda Giken Kogyo Kabushiki Kaisha, Tokyo (JP); Kabushikikaisha Tsukasa Sokken, Tokyo (JP)

( * ) Notice: Subject to any disclaimer, the term of this patent is extended or adjusted under 35 U.S.C. 154(b) by 0 days.

(21) Appl. No.: 09/923,435

(22) Filed: Aug. 8, 2001

(65) Prior Publication Data

US 2001/0049973 A1 Dec. 13, 2001

Related U.S. Application Data

(62) Division of application No. 09/310,342, filed on May 12, 1999, now Pat. No. 6,293,161.

(30) Foreign Application Priority Data

| | | | |
|---|---|---|---|
| May 12, 1998 | (JP) | | 10-129138 |
| May 12, 1998 | (JP) | | 10-129148 |
| Jun. 22, 1998 | (JP) | | 10-173747 |
| Jul. 14, 1998 | (JP) | | 10-199039 |
| Jul. 14, 1998 | (JP) | | 10-199040 |
| Sep. 16, 1998 | (JP) | | 10-261230 |

(51) Int. Cl.$^7$ ................................. G01N 1/00
(52) U.S. Cl. ..................................... 73/863.11
(58) Field of Search ...................... 73/864.51, 864.62, 73/864.63, 863.11, 864.33, 864.34, 864.73, 863.01–863.03, 23.31, 23.32

(56) References Cited

U.S. PATENT DOCUMENTS

| | | | | |
|---|---|---|---|---|
| 3,699,814 A | * | 10/1972 | Kaufman | 73/863.11 |
| 3,793,887 A | * | 2/1974 | Anderson et al. | 73/864.62 |
| 3,921,456 A | * | 11/1975 | Newcomb, Jr. et al. | 73/863.31 |
| 5,456,124 A | * | 10/1995 | Colvin | 73/863.11 |
| 6,114,178 A | * | 9/2000 | Dezael et al. | 73/863.11 |

* cited by examiner

*Primary Examiner*—Robert Raevis
(74) *Attorney, Agent, or Firm*—Birch, Stewart, Kolasch & Birch, LLP

(57) ABSTRACT

An exhaust gas sampling apparatus for analyzing the contents in exhaust gas. The sampling apparatus intakes air from an air intake conduit and mixes the air with exhaust gas taken from an exhaust gas supply conduit. The mixed gas can be sampled in different sampling conduits based upon the type of exhaust gas being examined. The apparatus includes heaters for heating various conduits to prevent condensation from forming within the conduits.

12 Claims, 8 Drawing Sheets

(a)

(b)

EXHAUST GAS SAMPLING APPARATUS

This application is a divisional of application Ser. No. 09/310,342, filed on May 12, 1999, the entire contents of which are hereby incorporated by reference and for which priority is claimed under 35 U.S.C. §120; and this application claims priority of application Ser. Nos. 10-129138, 10-129148, 10-199039, 10-173747, 10-199040, and 10-261230 filed in JAPAN on May 12, 1998, May 12, 1998, Jul. 14, 1998, Jun. 22, 1998, Jul. 14, 1998 and Sep. 16, 1998 under 35 U.S.C. §119, now U.S. Pat. No. 6,293,161.

BACKGROUND OF THE INVENTION

1. Field of the Invention

The present invention relates to an exhaust gas sampling apparatus for analyzing contents in exhaust gas from an automobile, a motorboat, a mowing machine and so on.

2. Description of Related Art

The construction of an exhaust gas sampling apparatus according to the conventional art will be explained by referring to FIG. 8. In the figure, reference numeral 201 indicates an intake air supply conduit for supplying fresh air from outside, an end of which is enlarged in the diameter thereof so as to form an air intake 202, in which is provided a filter 203. To the intake air supply conduit 201 is connected an exhaust gas supply conduit 204, and a gas mixture circulation conduit 205 is formed downstream from the connecting portion of the intake air supply conduit 201 and the exhaust gas supply conduit 204, and through the gas mixture circulation conduit 205, exhaust gas diluted with fresh air is extracted to the downstream side by a blower 206 provided in the downstream side thereof.

Here, the reason for mixing the exhaust gas with fresh air from outside when analyzing the contents of the above-mentioned exhaust gas lies in that there is a necessity to lower a ratio of moisture within the exhaust gas by mixing with fresh air, since otherwise dew drops will be condensed due to a decrease in the temperature on the way, when trying to send a pure sample of exhaust gas to an analyzer.

Interrupting the gas mixture circulation conduit 205 in the down-stream side from the connecting portion of the above-mentioned intake air supply conduit 201 and exhaust gas supply conduit 204, there is provided a mixing device 207, and further provided is a venturi device 208 down-stream of the mixing device 207, for the purpose of maintaining the exhaust gas at a constant flow rate, as a means of conforming to the different displacements and exhaust flow rates of various kinds of engines.

Further, from the gas mixture circulation conduit 205 is divided a sampling conduit 209, in the downstream side from the above-mentioned mixing device 207 but up-stream from the above-mentioned venturi device 208, and this sampling conduit 209 is further divided into three (3) conduits, to each of which is connected one of sampling bags 211 . . . through one of joints 210 . . . , respectively.

Further, from the air supply conduit 201 leads a reference air supply conduit 220, from the flow up-stream from the connecting portion with the exhaust gas supply conduit 204, and this reference air supply conduit 220 is also divided into three (3) conduits to be connected to the sampling bags 211 . . . through one of the joints 210 . . . , respectively.

Furthermore, a lead back conduit 230 being connected to the analyzer is connected to or closed from each one of the divided conduits 209a and 220a by means of valves 230a . . . , while an exhaust conduit 240 is also connected to or closed from each one of the divided conduits 209a and 220a by means of valves 240a, respectively. Still, valves 212 and 222 are provided in the up-stream side from the valves 230a and 240a for each one of the divided conduits 209a and 220a, and also a reversible pump 241 is provided in the flow of the exhaust conduit 240.

The analyzing method in such an exhaust gas sampling apparatus according to the conventional art, the structure of which is mentioned in the above, will be described below, in particular with reference to the sampling conduit 209.

First, the pump is driven under the condition where the valves 212 are turned OPEN while the valves 230a and 240a are CLOSED, so as to introduce the diluted exhaust gas into each of the sampling bags 211 according to a measuring mode, and then the valves 212 and 240a are turned CLOSED while the valves 230a are OPEN, so as to send the diluted exhaust gas into the analyzer through the lead back conduit 230, thereby measuring carbon monoxide (CO), hydrocarbon (HC), nitrogen compounds ($NO_x$) and so on in the exhaust gas, in accordance with the predetermined mode for measuring.

As such the measuring modes are already known as an LA-4 mode and a US06 mode, as per the regulations in the USA, for example. (There are also known a 10.15 mode and 11 mode, as per the domestic regulations in Japan.) Here, in accordance with the LA-4 mode, the contents in the exhaust gas are measured in each of the following time periods: (1) from starting of the engine up to a time point of a lapse of 504 sec., (2) from 505 seconds up to the time point of the lapse of 1,374 sec., and (3) from a re-starting after 10 minutes suspension of the engine up to the time point of the lapse of 504 sec. Accordingly, in the LA-4 mode, the exhaust gases during the above-mentioned intervals (1) to (3) must be collected into the sampling bags, respectively, and therefore there are prepared the three (3) pieces of the divided conduits and the three (3) bags.

Also, in accordance with the SU06 mode, in which the exhaust gas exhausted from the engine being at almost full throttle for ten (10) minutes is reserved or stored in the sampling bag to be analyzed, only one of the sampling bags is used according to this measuring mode.

In the case where the measurement of the above LA-4 mode is conducted with an ordinary gasoline engine, the flow rate is changed for each of the intervals (1) to (3) of the LA-4 mode, while suppressing the mixture with air to as low a ratio as possible, for obtaining correct measurement values. Therefore, because the gas mixture flowing within the gas mixture circulation conduit must be controlled to be from 3 to 9 $m^3$/min in the flow rate thereof, the above-mentioned venturi, of a variable flow rate type, is utilized.

Further, in the US06 mode, the gas mixture must be controlled at 21 $m^3$/min in the flow rate thereof.

FIG. 9(a) shows an enlarged cross sectional view taken along the direction of the flow in the venturi 208 of the variable flow rate type, and FIG. 9(b) shows an enlarged cross sectional view taken in the direction orthogonal to the direction of flow, wherein the cross sectional area of flow passage 252 at a neck portion 251 is changed by shifting an external wall or a core of the venturi in a relative manner, so as to control the flow rate through it.

When completing the measurement, the valves 212 and 230a are turned CLOSED while the valves 240a are OPEN, and air is sent into the sampling bags 211 by driving the reversible pump 241 of the exhaust conduit 240 into the reverse direction of rotation. Then, the reversible pump 241 is rotated in the forward direction to discharge the exhaust gas including the air within the sampling bag. The exhaust gas within the sampling bag is completely removed by repeating this operation, so as to be prepared for the next measurement.

In the exhaust gas sampling apparatus as mentioned above, an exhaust pipe of an automobile is connected to the exhaust gas supply conduit 204 and at the same time the blower 206 is driven, then the exhaust gas is diluted by mixing with the intake air, to a concentration wherein the mixture has a mass 20 times that of the exhaust gas constituent therein, so as to eliminate the condensation of water droplets due to the decrease in the temperature of the gas. After being sent through the sampling conduit 209, as well as the conduit divided therefrom, to be then stored in the bag 211, a portion of the exhaust gas is supplied to the analyzer to be analyzed.

However, when the exhaust gas exhausted from the engine is diluted to 20 times the mass thereof, it is difficult to obtain a correct result of the measurements. In particular, with an automobile of low pollution (emissions) installed with a lean bum gasoline engine which bums diluted fuel therein, the contents of the exhaust gas discharged from it is inherently near to those of the fresh air, and the drawback mentioned above is considerable.

Further, as the sampling conduit is used a conduit made from Teflon resin or that on which Teflon resin is coated, according to the conventional art. With this, however, pollution or soot is easily absorbed on the sampling conduit and also an ingredient of hydrocarbon is exuded from the Teflon resin, therefore it is unsuitable for use in the measurement of the emissions of an automobile of a low pollution type as discussed above.

Moreover, using sampling conduit 209 as an example, of the conventional art, when completing the predetermined sampling operations, the valves 230a are turned OPEN while keeping the valves 212 . . . in the CLOSED condition, and the reversible pump 241 is driven to rotate in the reverse direction so as to supply the air into the bags 211 . . . through the exhaust pipe 230, and thereafter, the reversible pump 241 is driven to rotate in the forward direction to discharge the gas from the bags. This is repeated several times so that no exhaust gas remains within the bags or the conduits connecting to the analyzer.

However, though conducting such air purging in the above-mentioned manner, the absolutely correct measurement value cannot be expected, since it is impossible to substitute the air for the exhaust gas remaining within the sampling conduit 209 at the side up-stream of the valves 212 . . . .

Furthermore, in the conventional art, the contents of the exhausts gas remaining within the conduits are removed by the air, however, since the contents contained in the exhaust gas are very small in quantity and are similar in composition to the fresh air, in particular in the case of the measurement for the low pollution car, no guarantee can be made of the correct measurement with such air purging.

Also, in the exhaust gas sampling apparatus of the conventional art, the analysis is made by connecting the sampling bags 211 to the conduits 209a . . . at the side of a main body thereof, therefore, the conduits must be elongated, which is troublesome in a case where the analyzer is located at a position far from the exhaust gas sampling apparatus. Further, on the passage thereof is generated the water condensation into which the contents of the exhaust gas dissolve, therefore, it is impossible to obtain a correct result of the analysis.

Even in the conventional apparatus, it is of course possible to divide the sampling bags 211 from the portion of the joints 210, however it is difficult to carry a large number of the bags, and there is a possibility of mistaking the bag in which the reference air is contained for the bag in which the diluted exhaust gas is contained to be measured.

Furthermore, even if it is possible to carry them, since the exhaust gas within the bags is cooled down during transport (flow) thereof through the conduits, causing water condensation, and into the condensation is dissolved the contents of the exhaust gas, it is therefore difficult to obtain the measurement correctly.

Also, the conventional apparatus includes a problem relating to the variable type of Venturi. In the conventional apparatus, for the purpose of decreasing the flow rate of the gas mixture, the core is shifted to the left-hand side in FIG. 9(a), so as to make the area of flow passage narrower. On the contrary, it is shifted to the right-hand side for increasing the flow rate, so as to widen the area of flow passage. For enabling both the measurement of the LA-4 mode and of the US06 mode, although it is theoretically adequate to set up the diameter size of the Venturi, in particular at the neck portion thereof, so that the flow rate of 21 $m^3$/min can be obtained under the condition of fall opening thereof, it is difficult, however, to throttle correctly if the diameter at the neck portion is large, and the control of the flow rate in the vicinity of 3 $m^3$/min comes to be difficult to achieve.

For this reason, in the case where the venturi of the variable flow rate type mentioned above is used, it is impossible to control the flow rate widely. Namely, the control of flow rate in the range from 3 to 21 $m^3$/min is difficult to achieve by use of only one of the venturi of the variable flow rate type.

As a means for solving the above problem, by providing a plurality of Venturis of a fixed flow rate type, it is possible to achieve the control of flow rate by exchanging the OPEN and CLOSED states therebetween, however when doing so, it is difficult to change the flow rate continuously therewith. For controlling it finely, the number of the venturis of the fixed flow amount types must be increased, and the structure thereof thus becomes complicated.

Furthermore, when providing the plurality of venturis of the fixed flow amount types, the flow rate becomes unstable when they are exchanged therebetween.

SUMMARY OF THE INVENTION

According to the present invention, for solving the first problem (i.e., the problem of condensation of moisture), there is provided an exhaust gas sampling apparatus, comprising: an exhaust gas supply conduit; an intake air supply conduit; a gas mixture circulation conduit being formed by joining said exhaust gas supply conduit and said intake air supply conduit; and a sampling conduit, being divided from the passage of said gas mixture circulation conduit, wherein a gas mixture to be analyzed is extracted through said sampling conduits, and wherein said exhaust gas supply conduit, said intake air supply conduit, said gas mixture circulation conduit, said sampling conduit, or a portion thereof where the gas mixture is stored temporarily is provided with a heater for preventing condensation of moisture in the exhaust gas.

With such a construction, though being diluted up to 20 times by mass with fresh air according to the conventional art, the condensation of moisture can be prevented, and may be prevented even with the dilution of 5 times by mass, thereby improving the accuracy in the analysis thereof.

Also, it is possible to provide a heat exchanger on said sampling conduit, at the down-stream side from the portion where said sampling conduit is divided, for decreasing the temperature of the exhaust gas, so as to protect a blower from damage thereby.

Further, it is also possible to provide a heater in said intake air supply conduit, in the side up-stream from the portion being joined with said exhaust gas supply conduit. With such a construction, it is possible to effectively prevent the exhaust gas from being decreased in the temperature thereof.

Further, said sampling conduit may be provided in plural systems thereof, depending upon kinds of engines. With such a construction, the conduit, in which remain the exhaust gas and the constituents (i.e., soot or the like) of the exhaust gas from the ordinary engine can be avoided to be re-used for the analysis of the exhaust gas from an engine of a low pollution car, thereby enabling accurate measurement Further, it is preferable to use the sampling conduit which is made from stainless steel. With the sampling conduit made from stainless steel, it is possible to prevent such drawbacks as the exuding of hydrocarbon from the conduit material, as occurs when heating the conduit made of Teflon, as well as providing for removal of any pollution or deposit therefrom easily, thereby increasing the accuracy in the measurement.

Furthermore, there is provided a lead back conduit, being connected between said sampling conduit and an analyzer, through which the exhaust gas to be analyzed flows, wherein said lead back conduit is able to introduce purging gas therein, thereby enabling increase in the accuracy of the measurement, compared to that of the conventional art. In particular, the purging gas is preferably nitrogen gas.

According to the present invention, for dissolving the second problem (i.e., the problem related to the sampling bags), there is provided an exhaust gas sampling apparatus for diluting exhaust gas with fresh air, storing the exhaust gas diluted into (a) sampling bag(s) once, and analyzing the stored diluted exhaust gas with an analyzer, comprising: a main body of a sampling apparatus; and a storage box, in which said sampling bags are positioned, being detachable from said main body of said sampling apparatus, wherein said storage box comprises: a connector unit for attaching and/or detaching the conduits on said main body of said sampling apparatus with the conduits within said storage box.

With such a construction, it is possible to move the large number of sampling bags at the same time, and also to connect the conduits with the analyzer with ease.

Also, it is preferable to provide a heater within said storage box. With provision of the heater, condensation of moisture within the exhaust gas to be analyzed can be prevented during the times of movement or waiting for analysis thereof.

Further, with provision of not only the heater but also of a temperature controller, it is possible to keep the temperature within the storage box constant, and further with installation of a battery within the storage box, it is also possible to keep the temperature within the storage box constant during the time of the moving.

Further, the above-mentioned connector unit can be constructed so that it holds a flexible conduit within said box in such a manner that it can be drawn out therefrom. With such a construction, a handling property thereof is improved.

Further, in the above-mentioned connector unit, it is also possible to form an opening(s) to blow out warm air held within said storage box to an outside thereof. With such a construction, it is possible to conduct the connection of conduits of the analyzer with the conduits drawn out from the box in warm atmosphere, so as to be free from condensation which would occur otherwise when connecting the conduits.

In particular, with provision of the connector unit being able to elevate up and down, it is possible to maintain the warm atmosphere in which the conduits are connected, so as to prevent occurrence of the condensation of moisture constituent in the exhaust gas.

According to the present invention, for solving the third problem (i.e., the problem related to the variable venturi), there is provided an exhaust gas sampling apparatus, comprising: an exhaust gas supply conduit; an intake air supply conduit; a gas mixture circulation conduit being formed by joining said exhaust gas supply conduit and said intake air supply conduit; a sampling conduit, being divided from said gas mixture circulation conduit and connecting to a passage thereof; and a venturi mechanism for controlling the flow rate of a gas mixture flowing within said gas mixture circulation conduit, wherein said venturi mechanism is constructed with a main venturi provided in line with said gas mixture circulation conduit, and a sub-venturi positioned in parallel with said main Venturi.

And, for example, in a case where said main venturi is a variable flow rate Venturi, and said sub-venturi a fixed flow rate venturi, the valve on the bypass passage is turned CLOSED in the LA-4 mode, while it is turned OPEN in the US06 mode, so as to conduct the sampling.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 9(b) is an enlarged cross sectional view thereof taken in the direction orthogonal to the direction of the flow.

DESCRIPTION OF THE PREFERRED EMBODIMENTS

Figure 1:
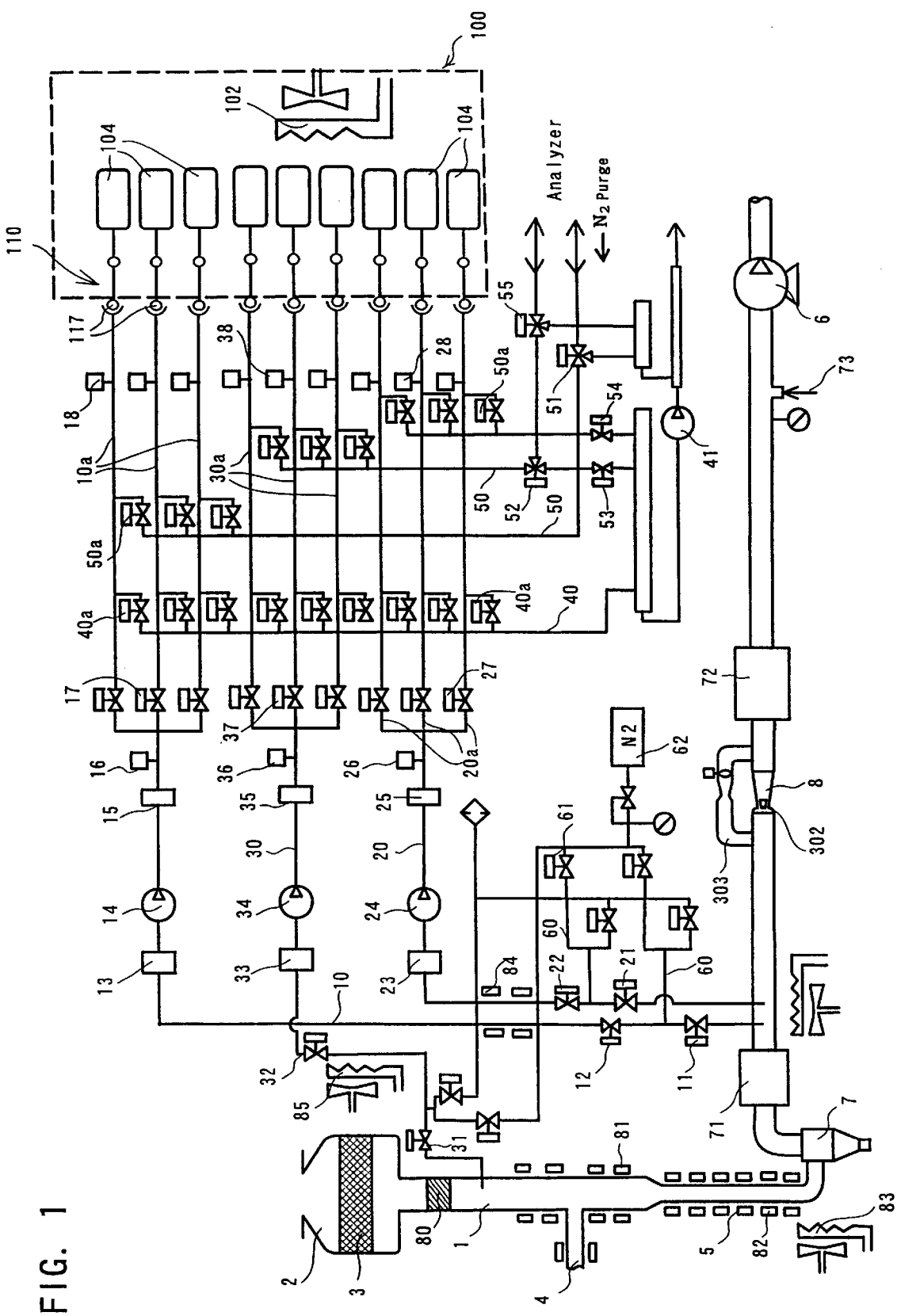
FIG. 1 is a view of showing the entire construction of an exhaust gas sampling apparatus according to the present invention.

Hereinafter, detailed explanation of the embodiments according to the present invention will be given by referring to the attached drawings. As shown in FIG. 1, with an exhaust gas sampling apparatus, an intake air inlet 2 is formed by expansion of one end of an intake air supply conduit 1, and within the intake air inlet 2 is provided a filter 3. Also, in line with the intake air supply conduit 1 is connected an exhaust gas supply conduit 4, wherein a gas mixture circulation conduit 5 is formed in the passage downstream starting from the connecting portion of the exhaust gas supply conduit 4, and through the gas mixture circulation conduit 5 is extracted the exhaust gas, being then diluted with fresh air while flowing to the downstream side by a blower 6 provided in the downstream thereof.

In line with the gas mixture circulation conduit 5 at the downstream side of the portion connecting with the exhaust gas supply conduit 4 there is provided a mixing device 7, and is further provided a venturi device 8 in the downstream of the mixing device 7, for the purpose of maintaining the flow of the exhaust gas at a constant rate as a means of adjusting for the different displacements and exhaust gas flow rates found in various kinds of engines.

Further, from the gas mixture circulation conduit 5, being downstream from the above-mentioned mixing device 7 but upstream of the above-mentioned venturi device 8, are divided two pieces of sampling conduit 10 and 20 comprised of stainless steel, and further, from the upstream portion of the joint portion between the above intake air supply conduit 1 and the exhaust gas supply conduit 4 is divided a secondary intake air supply conduit 30 comprised of stainless steel, for supplying the fresh air intake for the reference.

Between the two sampling conduits 10 and 20, the one sampling conduit 10 being used for the ordinary engine, and the other sampling conduit 20 being used for the engine of a car of a low-pollution gasoline-burning type, or the engine of a car burning natural gas.

The sampling conduit 10, being provided with valves 11, 12, a filter 13, a supply pump 14, a flow rate meter 15, and a pressure switch 16, is divided into three (3) conduits 10a . . . downstream of the pressure switch 16. On each of the divided conduits 10a . . . are provided valves 17 . . . and pressure switches 18 . . . , respectively.

Also, the sampling conduit 20, in use for the low pollution gasoline engine, being provided with valves 21 and 22, a filter 23, a supply pump 24, a flow rate meter 25 and a pressure switch 26, is divided into three (3) conduits 20a . . . downstream of the pressure switch 26. On each of the divided conduits 20a . . . are also provided valves 27 . . . and pressure switches 28 . . . , respectively.

Further, the secondary intake air supply conduit 30, to supply the reference fresh air, being provided with valves 31 and 32, a filter 33, a supply pump 34, a flow rate meter 35 and a pressure switch 36, is also divided into three (3) conduits 30a . . . downstream of the pressure switch 36. And, also on each of the divided conduits 30a . . . are provided valves 37 . . . and pressure switches 28 . . . , respectively.

Further, the passage between an exhaust conduit 40 and each of the divided conduits 10a . . . , and 30a . . . is connected or shut off by the corresponding valves 40a, and the exhaust conduit 40 is provided with a pump 41 at one end thereof.

Further, an analysis conduit 50 from each of the divided conduits 10a . . . of the sampling conduit 10 is selectively connected with the above-mentioned exhaust conduit 40 or the analyzer through a valve 51, while the analysis conduit 50 from each of the divided conduits 20a . . . of the sampling conduit 20 is selectively connected with the above-mentioned exhaust conduit 40 or the analyzer through the valves 52 and 53, and the analysis conduit 50 from each of the divided conduits 30a . . . of the secondary intake air supply conduit 30 is selectively connected with the above-mentioned exhaust conduit 40 or the analyzer through the valves 54 and 55.

Here, the analyzer connected with the analysis conduit 50 comprises an analyzer for an ordinary gasoline engine.

A nitrogen gas purging conduit 60 is connected to the downstream side of the valves 11 and 21 of the above-mentioned sampling conduits 10 and 20. In line with this nitrogen gas purging conduit 60 are provided valves 61 and a nitrogen gas bottle 62.

Further, downstream of the mixing device 7 of the above-mentioned gas mixture circulation conduit 5 is provided a heat exchanger 71 for maintaining at a constant the temperature of the gas mixture, and downstream of the venturi device 8 is provided another heat exchanger 72 for decreasing the temperature of the gas mixture flowing into the blower 6 so as to increase the service life thereof.

Further, to the gas mixture circulation conduit 5, between the heat exchanger 72 and the blower 6, an air supply conduit 73 is connected, for obtaining a further decrease in the temperature of the gas mixture, and from this air supply conduit 73 is introduced the fresh air of a controlled amount, increasing when the flow rate increases, by means of the venturi 8, so as to be sucked in with constant force without placing a load upon the blower 6.

Moreover, in the present embodiment, heaters are positioned at various places so as to prevent condensation of moisture that is constituent within the exhaust gas.

In more detail, within the intake air supply conduit 1 are positioned: a heater 80 in the side upstream from the joint portion with the exhaust gas supply conduit 4, a coil heater 81 around the joint portion between the intake air supply conduit 1 and the exhaust gas supply conduit 4, a coil heater 82 around the gas mixture circulation conduit 5 in the upstream side of the mixing device 7, an oven heater 83 in the vicinity of the mixing device 7, a coil heater 84 around the middle portions of the divided sampling conduits 10 and 20, and an oven heater 85 in the vicinity of the secondary intake air supply conduit 30, respectively.

Further, as will be mentioned later, in the vicinity of the sampling bags 104 is also positioned an oven heater 102.

Figure 2:
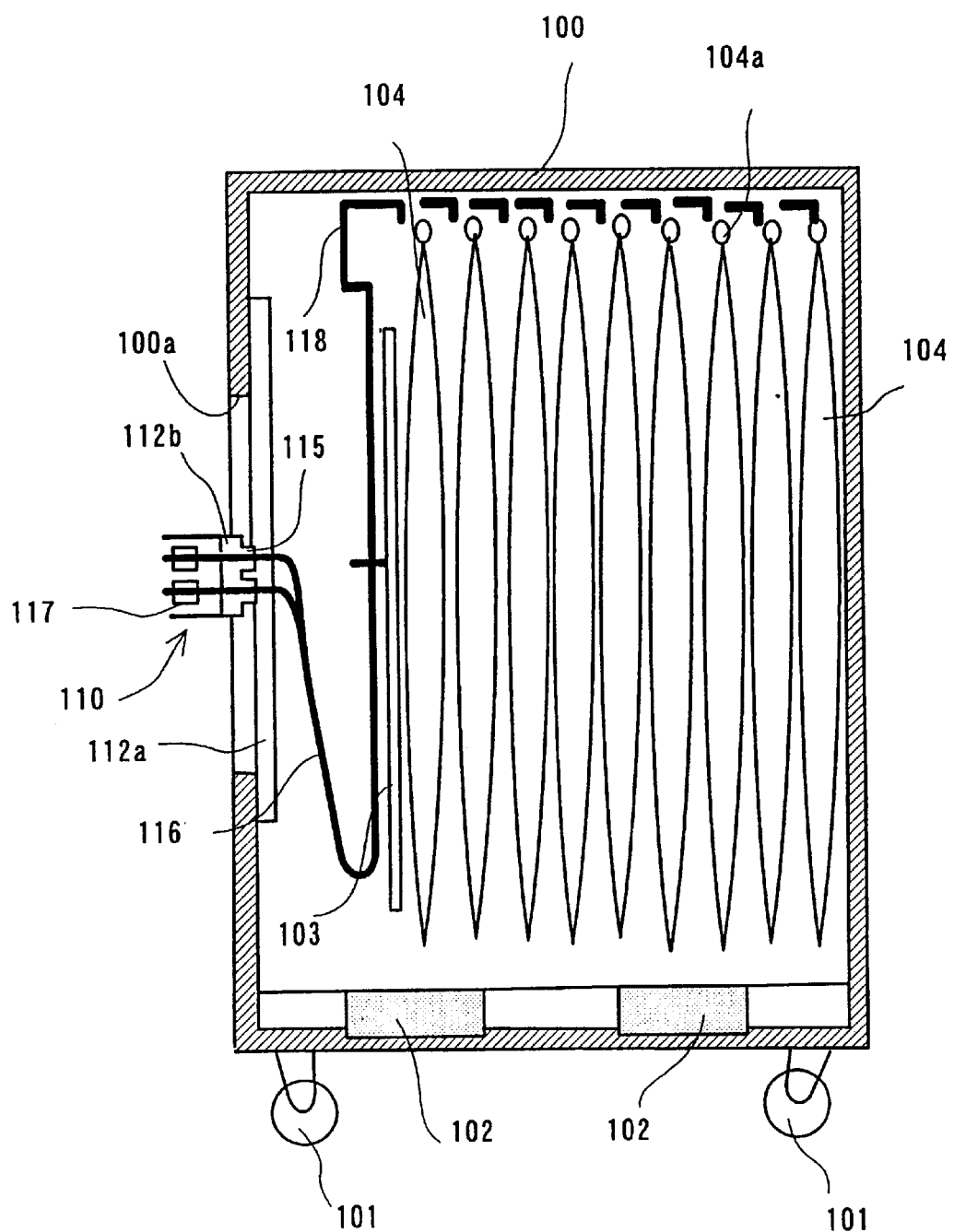
FIG. 2 is a front view showing the interior structure of a storage box for sampling bags.
Figure 4:
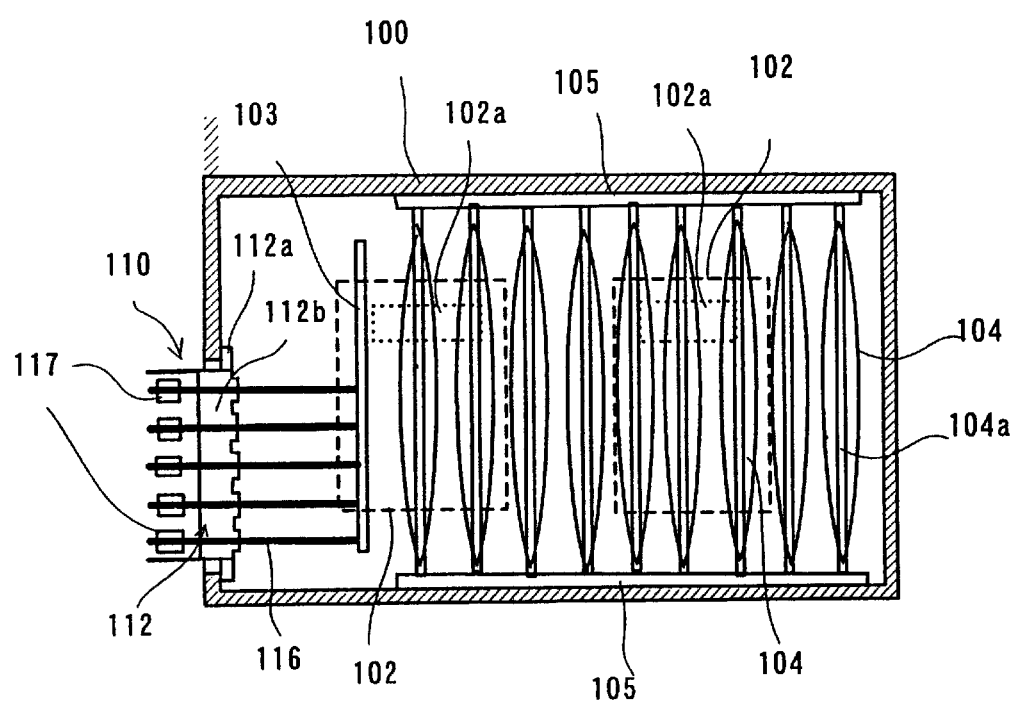
FIG. 4 is a plan view of the same storage box for the sampling bags.
Figure 5:
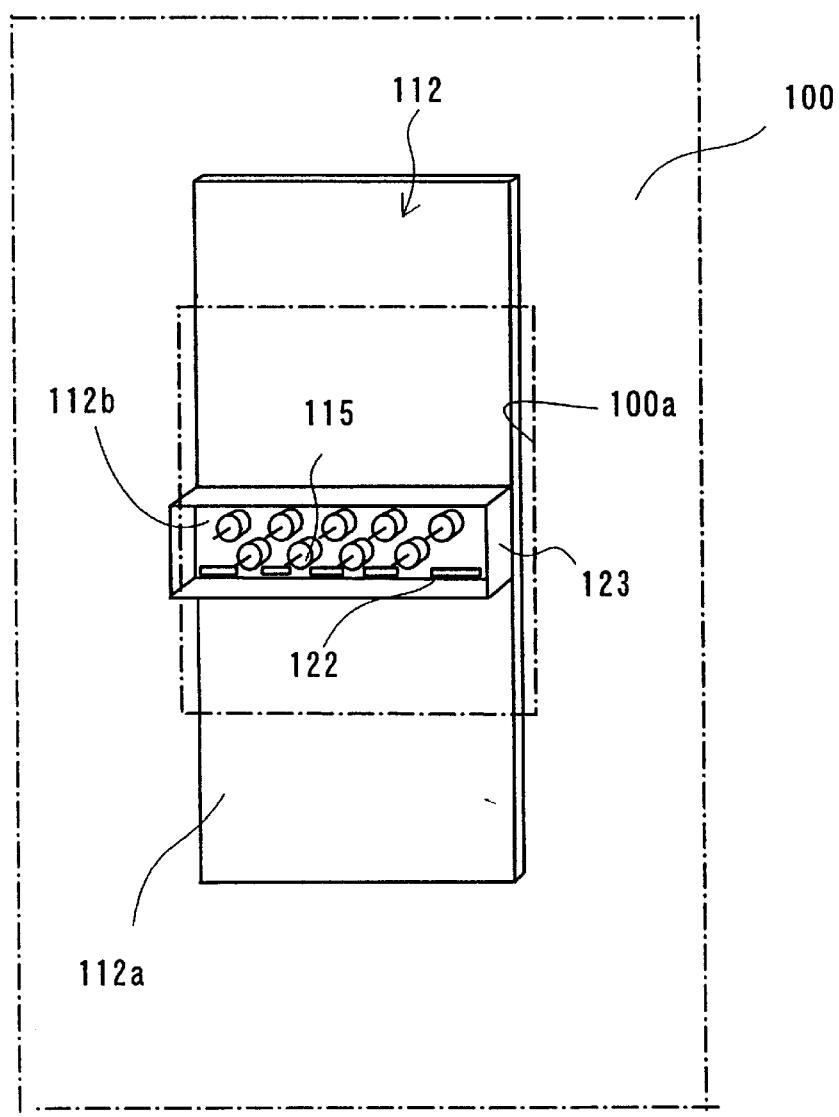
FIG. 5 is a perspective view of an elevating block.
Figure 6:
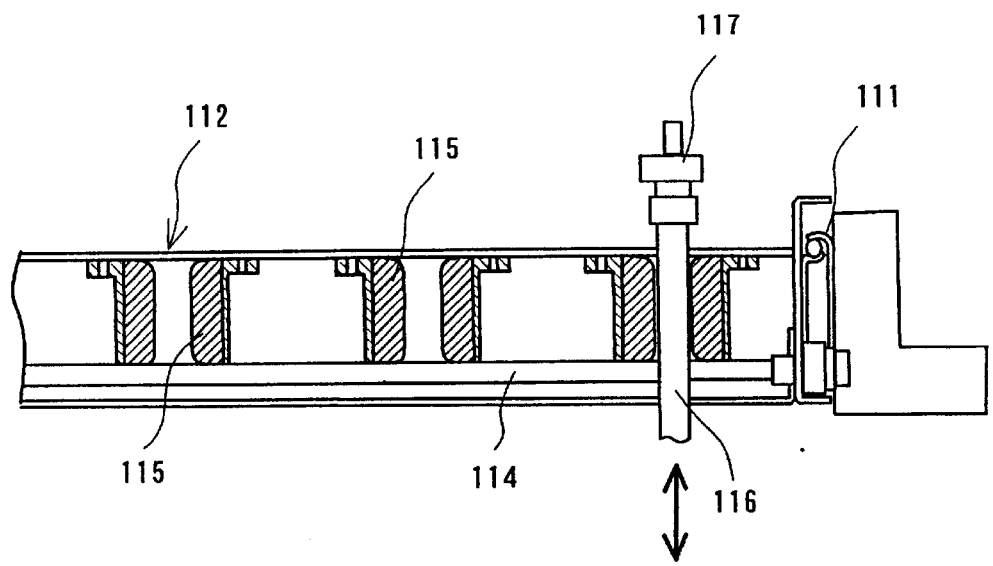
FIG. 6 is an enlarged view of a connector unit of the storage box for the sampling bags.

At the ends of the divided conduits 10a . . ., 20a . . . , and 30a . . . , a sampling bag storage box 100 is provided. The details of this sampling bag storage box 100 will be explained by referring to FIGS. 2 through 6. Here, FIG. 2 is a front view showing the interior structure of the sampling bag storage box, FIG. 3 is a side view of the same sampling bag storage box, FIG. 4 is a plane view of the same sampling bag storage box, FIG. 5 is a perspective view of an elevating block, and FIG. 6 is an enlarged view of the principle portion of a connector unit of the sampling bag storage box.

On the bottom surface of the storage box are attached casters 101 to provide for the storage box to be movable on a floor, and on the bottom portion within the storage box 100 is positioned the oven heater 102. In the vicinity of this heater 102 is provided a fan 102a to circulate warn air within the storage box 100, thereby keeping the atmosphere in the box at an uniform temperature and preventing the moisture contained in the exhaust gas to be analyzed from condensing.

Further, within the storage box 100 is provided a temperature controller 120 to keep the temperature within the storage box 100 at a temperature of about 40° C. For example, the heater 102 is turned ON or OFF when the temperature inside the storage box shifts beyond the pre-set upper and lower values thereof. Under the condition where the storage box 100 is attached with the main body of the sampling apparatus, an electric power source of, for instance, AC 100 V is accessed through a socket 121, while when the storage box 100 is separated or disconnected from the main body of the sampling apparatus to be moved, or during the time when the sample box is left waiting in an analysis room, the electric power source from a battery provided in the storage box 100 is used to power the heater 102.

Figure 3:
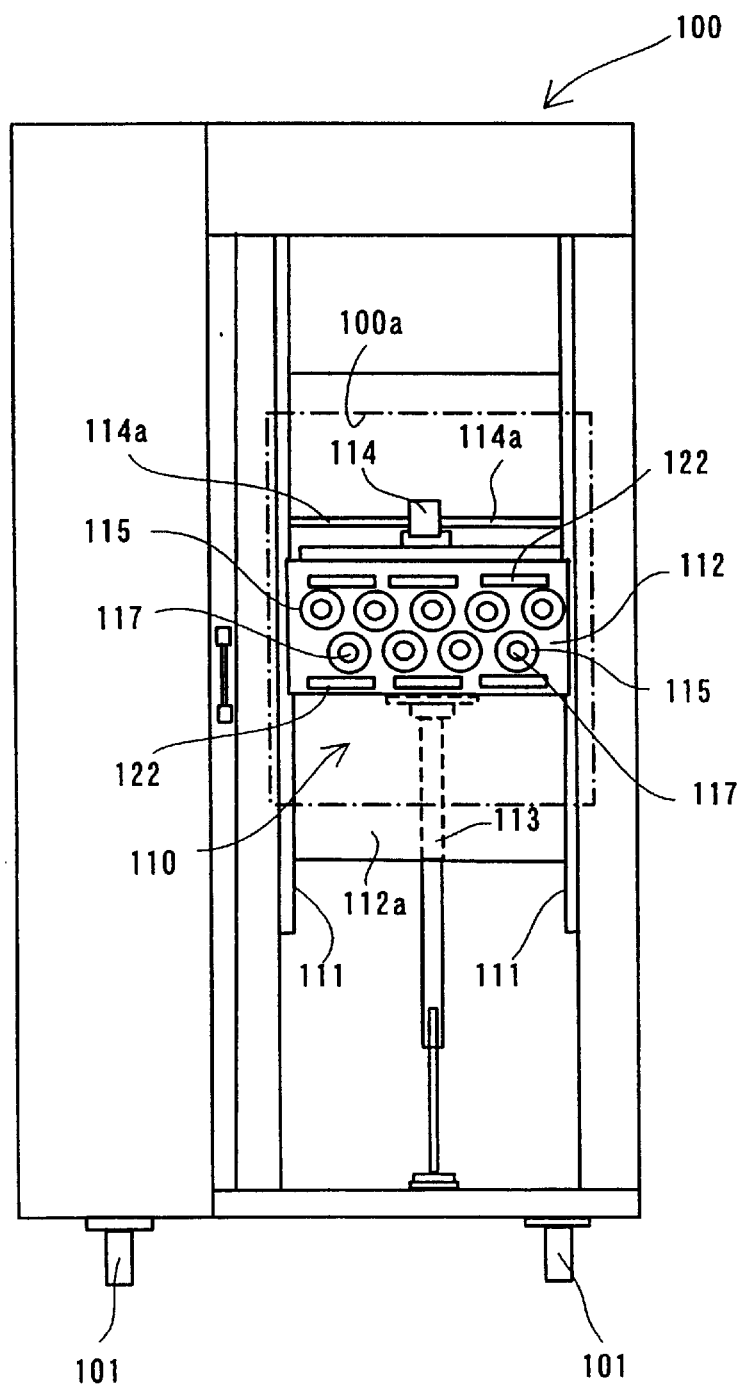
FIG. 3 is a side view of the same storage box for the sampling bags.

Also, the inside of the storage box 100 is divided into a right-hand-side space and a left-hand-side space by a partition plate 103, and within the wide space at the right-hand side in FIG. 3 can be stored the sampling bags 104 . . . in the total number of nine (9). Each of the sampling bags 104 is formed from material of fluorocarbon polymer having a low level of hydrocarbon (HC) generation.

Further, each sampling bag 104 is hung from one of bars 104a at the top end portion thereof, and the bars 104a are hooked on rails 105 provided on a ceiling of the storage box 100, so as to be able to be shifted in the horizontal direction.

At one side of the storage box 100 may be provided a connector unit 110. The connector unit 110 hooks an elevating block 112 on guide rails 111 elongated in the vertical direction.

The elevating block 112 comprises a plate 112a which is biased upward by a gas spring 113, and a guide holder 112b which is provided in the middle portion of the plate 112a in the direction of height thereof.

The upper limit of the elevating block 112 is regulated by a stopper 114. Namely, the stopper 114 comprises arms 114a and 114a at both the left-hand side and the right-hand side, and those arms 114a and 114a are biased in an expanding and opening direction by a spring provided at the center thereof.

In this manner, when the elevating block 112 is pushed, together with the stopper, upward against the biasing of the gas spring 113, the arms 114a and 114a are hooked on the concave portions formed in the rails 111 by means of the repelling force of the spring, thereby enabling fixture of the elevating block 112 at that position.

The above-mentioned plate 112a has such a size that it covers an opening 100a formed in the side surface of the storage box 100 even when it is shifted up and down, thereby preventing warm air held within the storage box 100 from leaking outside through the opening 100a.

Further, on a guide holder 112b projecting from the above-mentioned opening 100a are held guides 115 . . . in the same number as the number of the sampling bags 104. In each guide 115 is inserted a flexible conduit 116 of stainless steel in such a manner that it can be drawn out therefrom. At the tip of this flexible conduit 116 is attached a joint 117, and the base portion thereof is attached onto a joint provided on the above-mentioned partition plate 103. To this joint is connected one end of a fixed conduit 118 of stainless steel, and the other end of the fixed conduit 118 is connected with each of the sampling bags 104 through a Teflon pipe.

Further, in the periphery portion of the above-mentioned guide holder 112b are formed openings 122 . . . , and a hood 123 is provided projecting outwardly so as to surround the openings 122 . . . , thereby encircling the tips of the above-mentioned flexible conduits 116 within a space surrounded by the hood 123.

Figure 7:
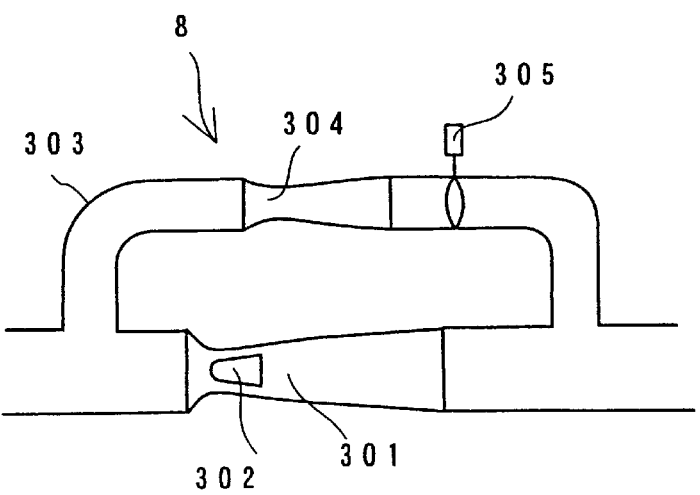
FIG. 7 is an enlarged view of a venturi device.
Figure 8:
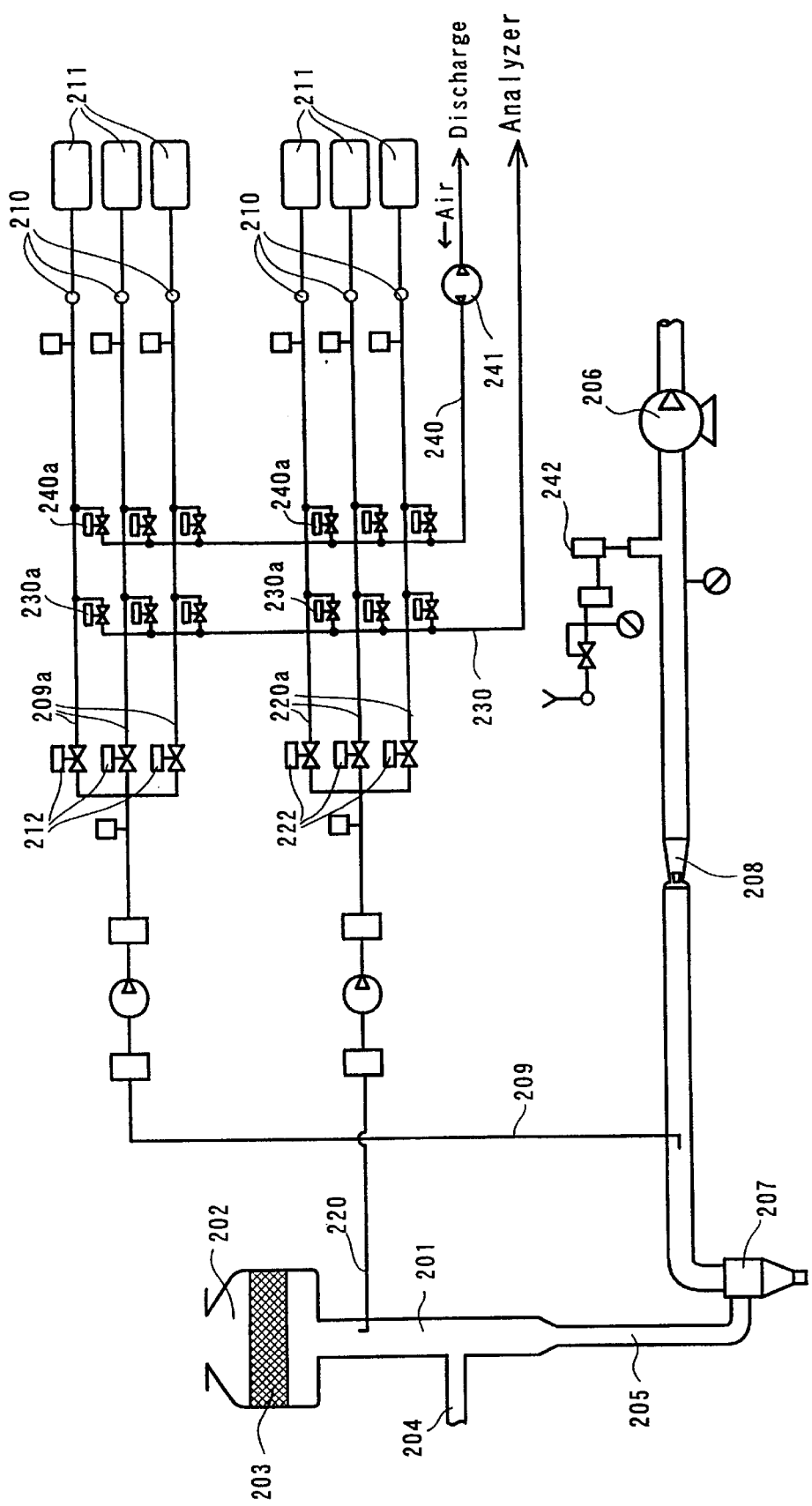
FIG. 8 is a view of showing the entire construction of the exhaust gas sampling apparatus according to the conventional art.
Figure 9:
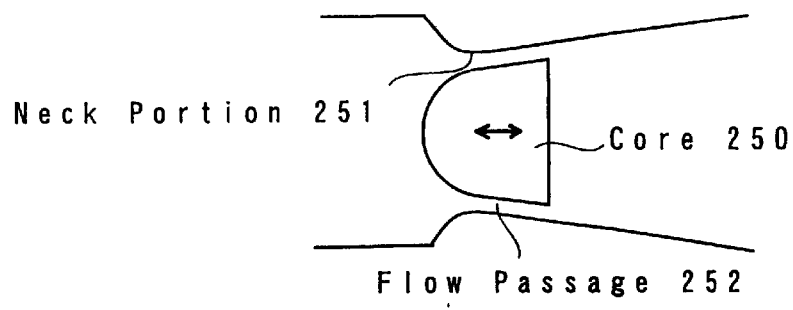
FIG. 9($a$) is an enlarged cross sectional view of a variable flow rate type venturi taken along the direction of flow therein.
Figure 9:
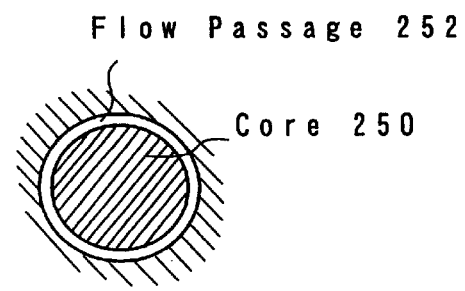

In the above-mentioned venturi device 8, as is shown in FIG. 7, a variable flow rate venturi 301 is provided as a main venturi in a portion of the gas mixture circulation conduit 5, and within the variable flow rate venturi 301 is provided a core 302 for adjusting the cross section area of the flow passage thereof. Further, in parallel to the variable flow rate venturi 301 is provided a bypass conduit 303, and in a portion of this bypass conduit 303 is provided a fixed flow rate venturi 304 as a sub venturi, and further in the downstream side of the fixed flow rate venturi 304 is provided a valve 305.

However, for the fixed flow rate venturi 304, the variable flow rate venturi may be provided in place thereof.

In the above, for analyzing the exhaust gas from an ordinary engine, after first confirming that the valves 21, 22, 27 . . . , 40a . . . , 50a . . . are turned CLOSED while the valves 11, 12, 17 . . . , 31, 32, 37 . . . are turned OPEN, the exhaust pipe of the car is connected to the exhaust gas supply conduit 4 and the blower 6 is driven. Further, the supply pump 13 is driven. After the exhaust gas and the intake fresh air are mixed by the mixing device 7, a portion of the gas mixture is stored in each of the sampling bags 104 . . . through the sampling conduit 10 as well as the divided conduits 10a . . . .

In the above, depending upon the displacement of the engine, for example, the core 302 of the variable flow rate venturi 301 is shifted so as to change the flow rate within the range from 3 to 15 m$^3$/min, thereby adjusting the dilution ratio of the gas mixture flowing into the sampling conduit 10.

Further, in parallel with the above, the supply pump 34 is driven, which is provided on the intake air supply conduit 30 for taking in fresh air for the reference. A portion of the introduced fresh intake air is also stored in each of the sampling bags 104 . . . through the divided conduits 10a . . .

Thereafter, by operating valve 51, valves 17 . . . and the valves 40a . . . are turned CLOSED while turning the valves 50a . . . OPEN under the condition that the analysis conduit 50 from the divided conduits 10a . . . is connected to the analyzer, so that the gas mixture to be analyzed, being stored within the bags 104, flows through the divided conduits 10a . . . in the reverse direction, thereby being sent into the analyzer to be analyzed therewith.

In the same manner, in parallel to the above, the valves 37 . . . and 40a . . . are turned CLOSED while the valves 50a . . . are turned OPEN, so that the intake fresh air for use as the reference, being stored within the bags 104, also flows through the divided conduits 30a . . . in the reverse direction, thereby being sent into the analyzer which is attached to the main body of the sampling apparatus to be analyzed therewith.

It is possible to know the ratio of the contents (for example, nitrogen oxide) being inherently contained within the intake fresh air by analyzing the intake air for use as the reference, therefore, the amount of nitrogen oxide, etc., which are created by combustion, can be detected correctly, by subtracting the reference values, thus adjusting by calculation the analyzing result for the gas mixture.

Also, in a case of analyzing the contents within the exhaust gas from an engine which burns natural gas, for example, by turning the valve 11 of the sampling conduit 10 CLOSED, while turning the valve 21 of the sampling conduit 20 OPEN, the collection of the exhaust gas is conducted in the same manner as mentioned in the above, and then, is analyzed by means of an analyzer provided for exclusive use in analyzing natural gas engine exhaust, which is separately provided.

After sampling, the joints 117 are disjoined from the respective divided conduits 10a . . . , 20a . . . and 30a . . . so as to allow movement of the storage box 100 into the analysis room. Then, the joints 117 are connected to the respective conduits of the analyzer to conduct the analyzing therewith.

On the other hand, when conducting the analysis of the USOG mode, the valve 305 of the bypass conduit 303 is turned OPEN so as to obtain the flow rate from 20 to 21 $m^3$/min of the mixture gas. Then, the collection of the exhaust gas is conducted in the same manner as mentioned in the above, by using only one of three (3) pieces of the divided conduits 10a, and the gas mixture to be analyzed, being stored within the bags 104, flows through the divided conduits 10a . . . in the reverse direction, thereby being sent into the analyzer to be analyzed therewith.

Also, in a case of analyzing the constituents of exhaust gas from an engine which burns natural gas, for example, by turning the valve 21 of the sampling conduit 20 CLOSED, while tuning the valve 31 of the secondary intake air supply conduit 30 OPEN, the collection of the exhaust gas is conducted in the same manner as mentioned in the above, and then is analyzed by means of an analyzer which is in exclusive use for analyzing emissions of natural gas powered engines, which is separately provided.

However, since the flexible conduits 116 can be drawn out from the guide 115 when connecting the joints 117 to the respective conduits of the analyzer, the operation of connection thereof can be performed easily.

Further, condensation of moisture can be prevented by warming the sampling bags 104 during any moving and waiting prior to analysis, by means of the heater 102.

In the operation of the connection, since the air inside the storage box 100 is kept at a relatively high temperature (approximately 40° C.) by means of the heater 102, the connecting operation can be performed while keeping the contained air at the relatively high temperature, while blowing warm air held within the storage box 100 toward each of the conduits of the analyzer. With this system, the condensation of moisture in the exhaust gas can be prevented.

Even when the height of the conduits of the analyzer changes depending upon each of types thereof, it is possible to keep warm the atmosphere surrounding the connecting operation, by adjusting the height of the opening 122 to that of the conduits through the adjustment in the height of the elevating guide holders 112b.

As is explained in the above, according to the present invention, since the heaters are provided on the periphery of the main conduits comprising the exhaust gas sampling apparatus, the exhaust gas can be released or protected from abrupt decrease in the temperature even if the mixture ratio with the intake air is set to be small, i.e., the dilution ratio is set to be small, thereby preventing condensation of moisture therein.

Accordingly, the constituents of the exhaust gas are inhibited from dissolving into the condensed moisture and an analysis result showing the value being less than the actual ratio is avoided, thereby increasing the reliability in the result of the measurement.

Further, with provision of the heat exchangers at the predetermined positions, it is possible to keep the gas mixture which is supplied to the sampling conduits at a constant temperature, or also to elongate the service life of the blower.

Further, the intake air supply conduit for use as a passage for the reference is divided from the intake air supply conduit at a point upstream of the portion joining with the supply conduit for the exhaust gas, therefore accurate analysis can be performed even if fluctuation occurs in the contents of the fresh intake air, and further, by providing the sampling conduits in plural systems thereof, it is possible to cope with the plural types of engines being different in the burning modes therein.

Further, the sampling conduit, being made from stainless steel, is hardly adhered with pollution or deposits thereon nor exudes hydrocarbon therefrom, therefore is also suitable for the measurement of the exhaust gas from a low pollution car.

Furthermore, after completing the sampling, by substituting nitrogen gas or the like for the gas within at least the sampling conduit and the analysis conduit, it is possible to conduct the accurate measurement, thereby increasing the reliability in the measured value.

Further, in the sampling apparatus according to the present invention, the sampling bags are stored inside the storage box, the box being detachable from the sampling apparatus, and thus the large number of bags can be moved easily to an analysis room located at a place being separated and/or far from the sampling apparatus, and also the storage box has a self-contained connector unit, therefore, the measurement can be performed by connecting the conduits held within the storage box directly to an analyzer, without taking the bags out of the storage box.

Further, with the provision of the heater inside the storage box, condensation of moisture in from the exhaust gas in the bags can be prevented, thereby enabling performance of accurate analysis Also, the portions of the conduits provided within the storage box are flexible conduits, each of which can be drawn from the connector unit, therefore, the piping operation at the main body side of the sampling apparatus, as well as the connecting and disconnecting operations with the conduits at the analyzer side become easy.

Furthermore, by letting warm air blow out from the connector, the occurrence of condensation can be prevented when connecting the conduits at the analyzer side, and further with provision of the elevating block in the connector, whereby are provided the openings through which to blow the warm air, it is possible to cope with a range of positions in terms of the height of the conduits at the analyzer side.

Also, the exhaust gas sampling apparatus, according to the present invention, comprises a venturi mechanism for controlling the flow rate of the gas mixture in the exhaust gas sampling apparatus, being constructed with a main venturi provided on the way of the gas mixture circulation conduit and a sub venturi positioned in parallel to the main Venturi, wherein at least one of those Venturis is the variable flow rate Venturi, thereby achieving the control of the flow rate in the gas mixture within a wide range.

Further, mechanically, since it is enough only to add the bypass conduit and the sub venturi which is provided on the bypass conduit, the present invention can be applied to an existing equipment or facility.

What is claimed is:

1. An exhaust gas sampling apparatus for analyzing exhaust gas, diluting the exhaust gas with intake fresh air, storing the exhaust gas diluted into a sampling bag once, and analyzing the diluted exhaust gas stored by means of an analyzer, comprising:
   a main body of a sampling apparatus; and
   a storage box, in which said sampling bag is positioned, being detachable with said main body of said sampling apparatus, wherein said storage box further includes
   a connector unit for attaching and detaching a plurality of conduits on said main body of said sampling apparatus with a plurality of conduits within said storage box, and
   a flexible conduit provided within said storage box and held in said connector unit in such a manner that it can be drawn out therefrom.

2. The exhaust gas sampling apparatus as defined in claim 1, wherein said flexible conduit is made from stainless steel.

3. The exhaust gas sampling apparatus as defined in claim 2, wherein said flexible conduit further comprises a tip, said tip being attached to a joint provided on a partition plate.

4. An exhaust gas sampling apparatus as defined in claim 1, wherein said storage box further comprises a heater and a temperature controller therein for maintaining a constant temperature of an inside of said storage box.

5. An exhaust gas sampling apparatus as defined in claim 4, said temperature controller maintaining a constant temperature of an inside of said storage box, said storage box further comprising a battery for driving said heater.

6. An exhaust gas sampling apparatus for analyzing exhaust gas, diluting the exhaust gas with intake fresh air, storing the exhaust gas diluted into a sampling bag once, and analyzing the diluted exhaust gas stored by means of an analyzer, comprising:
   a main body of a sampling apparatus; and
   a storage box in which said sampling bag is positioned being detachable with said main body of said sampling apparatus, wherein said storage box further includes a connector unit for attaching and detaching a plurality of conduits on said main body of said sampling apparatus with a plurality of conduits within said storage box, and
   an opening being formed in said connector unit through which to blow out warm air held within said storage box to an outside therefrom.

7. An exhaust gas sampling apparatus for analyzing exhaust gas, diluting the exhaust gas with intake fresh air, storing the exhaust gas diluted into a sampling bag once, and analyzing the diluted exhaust gas stored by means of an analyzer, comprising:
   a main body of a sampling apparatus; and
   a storage box in which said sampling bag is positioned being detachable with said main body of said sampling apparatus, wherein said storage box further includes
   a connector unit for attaching and detaching a plurality of conduits on said main body of said sampling apparatus with a plurality of conduits within said storage box,
   an elevating block in said connector unit and on which a flexible conduit provided within said storage box is held in such a manner that it can be drawn out therefrom, and
   an opening being formed through which to blow out warm air held within said storage box to an outside therefrom.

8. The exhaust gas sampling apparatus as defined in claim 7, wherein said elevating block further comprises a plate being biased upward by a gas.

9. The exhaust gas sampling apparatus as defined in claim 8, wherein said elevating block further comprises a guide holder which is provided in a middle portion of the plate.

10. The exhaust gas sampling apparatus as defined in claim 9, wherein said elevating block is further regulated by a stopper, said stopper further comprises arms provided at both a left-hand side space and a right-hand side space.

11. An exhaust gas sampling apparatus for analyzing exhaust gas, diluting the exhaust gas with intake fresh air, storing the exhaust gas diluted into a at least one sampling bag, and analyzing the diluted exhaust gas stored by means of an analyzer, comprising:
    a main body of a sampling apparatus, said main body including main body sampling conduits; and
    a storage box being detachably connected to said main body, said at least one sampling bag positioned within said storage box and said storage box further including
    a connector unit for attaching and detaching the main body conduits,
    storage box sampling conduits within said storage box, said storage box sampling conduits being detachably connected through said connector unit to said main body conduit, said storage box including casters, said casters permitting movement of said storage box with respect to said main body, and said least one sampling bag being mounted from a bar positioned at a top portion of said storage box,
    a right-hand side space and a left-hand side space,
    a partition plate being positioned between said right-hand side space and said left-hand side space,
    a heater being provided within said storage box, and
    a temperature controller for maintaining a constant temperature of an inside of said storage box.

12. The exhaust gas sampling apparatus as defined in claim 11, wherein said at least one sampling bag is formed from a fluorocarbon polymer material having a low level of hydrocarbon generation. spring.

* * * * *